United States Patent
Spiekermann et al.

(10) Patent No.: US 10,889,855 B2
(45) Date of Patent: *Jan. 12, 2021

(54) DETECTION OF NUCLEIC ACID MOLECULES

(71) Applicant: miRdetect GmbH, Bremen (DE)

(72) Inventors: Meike Spiekermann, Bremen (DE); Nina Winter, Hambergen (DE); Inga Flor, Bremen (DE); Gazanfer Belge, Bremen (DE)

(73) Assignee: miRdetect GmbH, Bremen (DE)

( * ) Notice: Subject to any disclaimer, the term of this patent is extended or adjusted under 35 U.S.C. 154(b) by 69 days.

This patent is subject to a terminal disclaimer.

(21) Appl. No.: 15/567,921

(22) PCT Filed: Apr. 29, 2016

(86) PCT No.: PCT/EP2016/059604
§ 371 (c)(1),
(2) Date: Oct. 19, 2017

(87) PCT Pub. No.: WO2016/174199
PCT Pub. Date: Nov. 3, 2016

(65) Prior Publication Data
US 2018/0163264 A1 Jun. 14, 2018

(30) Foreign Application Priority Data

Apr. 29, 2015 (DE) .................. 10 2015 106 646
Nov. 18, 2015 (EP) ...................... 15195182

(51) Int. Cl.
*C12Q 1/6851* (2018.01)
*C12Q 1/6886* (2018.01)
*C12Q 1/686* (2018.01)
*C12Q 1/6883* (2018.01)

(52) U.S. Cl.
CPC .......... *C12Q 1/6851* (2013.01); *C12Q 1/686* (2013.01); *C12Q 1/6883* (2013.01); *C12Q 1/6886* (2013.01); *C12Q 2600/158* (2013.01); *C12Q 2600/178* (2013.01)

(58) Field of Classification Search
CPC ........ C12Q 2600/158; C12Q 2600/178; C12Q 1/6851; C12Q 2531/113; C12Q 2545/114; C12Q 1/686
See application file for complete search history.

(56) References Cited

FOREIGN PATENT DOCUMENTS

CN 101363057 2/2009

OTHER PUBLICATIONS

Semmelmann, K. et al., miRNA biomarker discovery-overcoming limiting sample material, Qiagen Scientific Article, pp. 1-12 (Year: 2013).*
Human miRNome miScript miRNA PCR Array Product Sheet, pp. 1-21 (Year: 2013).*
Exiqon Data Analysis Guide for the miRCURY LNA™ Universal RT microRNA Ready-to-Use PCR panels using Exiqon GenEx software Version 2.5, pp. 1-53 (Year: 2013).*
Anandaram, H., Computational Analysis of Expression Based Regulation in Psoriasis: An Approach of Systems Biology to Understand Disease Pathology and Predict Potential Regulators, J. Sys. Biol. Res., vol. 1, pp. 1-17 (Year: 2017).*
International Search Report & Written Opinion, International Application No. PCT/EP2016/059604, dated Jul. 19, 2016, 14 pages.
Korenkova et al., "Pre-amplification in the context of high-throughput qPCR gene expression experiment," BMC Molecular Biology 16(5):1-10, 2015.
Mengual et al., "Multiplex preamplification of specific cDNA targets prior to gene expression analysis by TaqMan Arrays," BMC Research Notes 1(21):1-8, 2008.
Murray et al., "A pipeline to quantify serum and cerebrospinal fluid micro RNAs for diagnosis and detection of relapse in paediatric malignant germ-cell tumours," British Journal of Cancer 114:151-162, 2016.
Qiagen, miScript miRNA PCR Array Handbook, May 2012, 60 pages.
Qiagen, "miScript PreAmp Handbook," Aug. 2012, 52 pages.
Spiekermann et al., "MicroRNA miR-371a-3p in serum of patients with germ cell tumours: evaluations for establishing a serum biomarker," Andrology 3:78-84, 2015.
Chen et al. (2009) "Reproducibility of quantitative RT-PCR array in miRNA expression profiling and comparison with microarray analysis," BMC Genomics 10(407): 1-10.

* cited by examiner

*Primary Examiner* — Teresa E Strzelecka
(74) *Attorney, Agent, or Firm* — Leydig, Voit & Mayer, Ltd.; Tony Sanny; Gary Chapman

(57) ABSTRACT

The present invention relates to methods for the detection of nucleic acid molecules at the lower detection limit.

17 Claims, 2 Drawing Sheets

DETECTION OF NUCLEIC ACID MOLECULES

CROSS-REFERENCE TO RELATED APPLICATIONS

This application is a U.S. National Stage Application under 35 U.S.C. § 371 of International Application No. PCT/EP2016/059604, filed Apr. 29, 2016, which claims the benefit of and priority to German Patent Application 10 2015 106 646.7, filed Apr. 29, 2015, and European Patent Application No. 15195182.9, filed Nov. 18, 2015. Each of these applications is hereby incorporated by reference in its entirety.

TECHNICAL FIELD OF THE INVENTION

The present invention relates to methods for the detection of nucleic acid molecules at the lower detection limit.

BACKGROUND OF THE INVENTION

The expression level of specific nucleic acid molecules in biological samples taken from a test subject may be an indicator for the presence, absence and/or the extent of particular diseases or disorders.

For example, the generation of microRNA (miRNA) expression profiles has shown that in different diseases clear variations in the expression of specific miRNAs between healthy test persons and patients are present. miRNAs are short, highly conserved, non-coding RNAs, which play an important role in the complex network of gene regulation. They specifically bind to messenger RNAs (mRNAs) and control gene expression through regulation of mRNA stability and translation. Generally, miRNAs consist of 21 to 23 nucleotides.

Many diagnostically relevant nucleic acid molecules, e.g., specific miRNAs, are difficult to quantify accurately because of both their small size and their typically low concentrations in biological samples.

To detect the expression level of a specific miRNA, miRNA is usually isolated from the biological sample and reverse transcribed into synthetic DNA (cDNA). Afterwards the miRNA expression level is determined using quantitative real-time PCR (qRT-PCR). In some cases, a preamplification step is performed before the actual measurement. This additional step is done, if (i) not enough miRNA raw material for the use in several molecular biological determination methods (real-time PCR, micro arrays etc.) exists, and/or (ii) the concentration of miRNA in the sample is too low (i.e., without preamplification no signal would be generated during real-time PCR).

However, as shown below in comparative example 1, this 'classical' approach does not allow for the exact and reliable determination of expression levels if the target nucleic acid molecules are present in amounts at the lower detection limit, e.g., less than 1000 molecules per sample.

Accordingly, it was an object of the present invention to provide methods that facilitate the exact and reliable determination of the expression level of specific nucleic acid molecules, e.g., miRNAs, in biological samples at the lower detection limit.

SUMMARY OF THE INVENTION

In one aspect, the present invention relates to a method of determining the expression level of a specific nucleic acid molecule in a biological sample, the method comprising the steps of:

(i) providing a batch A comprising DNA or cDNA isolated/obtained from the biological sample;
(ii) providing three or more aliquots of batch A provided in step (i) and performing an independent polymerase chain reaction (PCR) with each of the three or more aliquots in order to amplify the specific nucleic acid molecule, thereby providing three or more batches B comprising the amplified specific nucleic acid molecule; and
(iii) mixing equal amounts of the three or more batches B, thereby providing a batch C, and determining the level of the specific nucleic acid molecule in batch C by a PCR-based approach, wherein the level determined in step (iii) corresponds to the expression level of the specific nucleic acid molecule in the biological sample.

In another aspect, the present invention relates to method of determining the expression level of a specific nucleic acid molecule in a biological sample, the method comprising the steps of:

(i) providing a batch A comprising DNA or cDNA isolated/obtained from the biological sample;
(ii) providing three or more aliquots of batch A provided in step (i) and performing an independent polymerase chain reaction (PCR) with each of the three or more aliquots in order to amplify the specific nucleic acid molecule, thereby providing three or more batches B comprising the amplified specific nucleic acid molecule; and
(iii) determining the level of the specific nucleic acid molecule in each of the three or more batches B by a PCR-based approach, wherein the mean value of the levels determined in step (iii) corresponds to the expression level of the specific nucleic acid molecule in the biological sample.

In one embodiment, the concentration of the specific nucleic acid molecule in the biological sample is $\leq 1 \times 10^{-11}$ M, or $\leq 1 \times 10^{-12}$ M, or $\leq 1 \times 10^{-13}$ M, or $\leq 1 \times 10^{-14}$ M, or $\leq 1 \times 10^{-15}$ M, or $\leq 1 \times 10^{-16}$ M.

In one embodiment, the concentration of the specific nucleic acid molecule in the biological sample is between $1 \times 10^{-11}$ M and $1 \times 10^{-17}$ M, or $1 \times 10^{-12}$ M and $1 \times 10^{-17}$ M, or $1 \times 10^{-13}$ M and $1 \times 10^{-17}$ M, or $1 \times 10^{-14}$ and $1 \times 10^{-17}$ M, or $1 \times 10^{-15}$ and $1 \times 10^{-17}$ M, or $1 \times 10^{-16}$ and $1 \times 10^{-17}$ M.

In one embodiment, the specific nucleic acid molecule is selected from the group consisting of a specific miRNA, a specific cell-free circulating DNA (e.g., a specific cell-free circulating tumor DNA), a specific mRNA, a specific siRNA and a specific snRNA.

In one embodiment, the specific nucleic acid molecule is a specific miRNA.

In one embodiment, the specific miRNA molecule is selected from the group consisting of miR-371a-3p, miR-93-5p, miR-372, miR-373, miR-367 and miR-20a-5p.

In one embodiment, the biological sample is selected from the group consisting of body fluid, tissue, cells, cell lysate and cell culture supernatant.

In one embodiment, the body fluid is selected from the group consisting of blood serum, blood plasma, seminal plasma, hydrocele fluid, spermatocele fluid, whole blood, urine, amniotic fluid, exudate, sputum, saliva and cerebrospinal fluid.

In one embodiment, the tissue is selected from the group consisting of native tissue, snap-frozen tissue and formalin-fixed and paraffin-embedded (FFPE) tissue.

In one embodiment, the tissue is tumor tissue.

In one embodiment, batch A comprises cDNA isolated/obtained from the biological sample.

In one embodiment, step (i) comprises the steps of:
(ia) isolating RNA from the biological sample; and
(ib) converting the RNA isolated in step (ia) into cDNA, thereby providing batch A comprising the cDNA.

In one embodiment, in step (ii), three aliquots of batch A are provided.

In one embodiment, the PCR-based approach is quantitative real-time PCR (qRT-PCR) or digital PCR (dPCR).

DETAILED DESCRIPTION OF THE INVENTION

Figure 1:
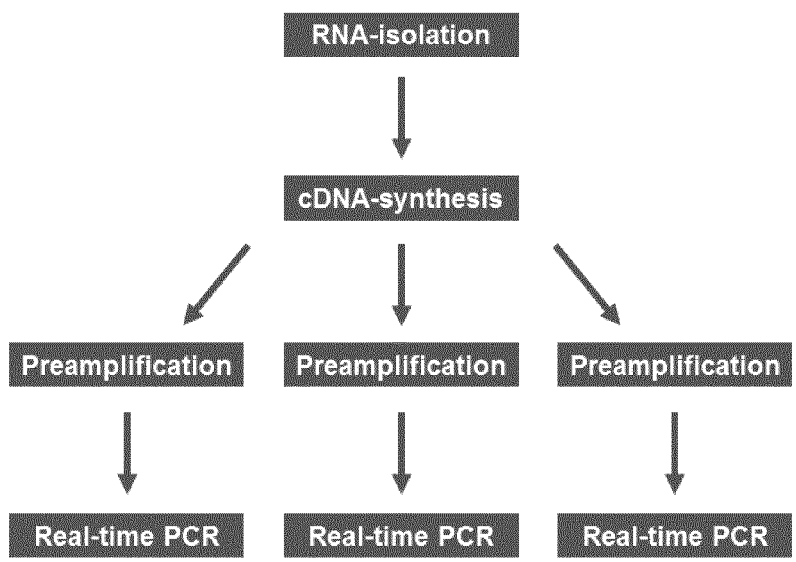
FIG. 1 shows a schematic representation of a method in accordance with the present invention (Example 1). Subsequent to three qRT-PCRs, the arithmetic mean value is calculated for the evaluation of the data.

Although the present invention is described in detail above and below, it is to be understood that this invention is not limited to the particular methodologies, protocols and reagents described herein as these may vary. It is also to be understood that the terminology used herein is for the purpose of describing particular embodiments only, and is not intended to limit the scope of the present invention, which will be limited only by the appended claims. Unless defined otherwise, all technical and scientific terms used herein have the same meanings as commonly understood by one of ordinary skill in the art.

In the following, certain elements of the present invention will be described. These elements may be listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments, which combine the explicitly described embodiments with any number of the disclosed and/or preferred elements. Furthermore, any permutations and combinations of all described elements in this application should be considered disclosed by the description of the present application unless the context indicates otherwise.

Preferably, the terms used herein are defined as described in "A multilingual glossary of biotechnological terms (IUPAC Recommendations)", H. G. W. Leuenberger, B. Nagel, and H. Kölbl, Eds., Helvetica Chimica Acta, CH-4010 Basel, Switzerland, (1995).

The practice of the present invention will employ, unless otherwise indicated, conventional methods of chemistry, biochemistry, cell biology, immunology, and recombinant DNA techniques which are explained in the literature in the field (cf., e.g., Molecular Cloning: A Laboratory Manual, 3$^{rd}$ Edition, J. Sambrook et al. eds., Cold Spring Harbor Laboratory Press, Cold Spring Harbor 2000).

Throughout this specification and the claims which follow, unless the context requires otherwise, the word "comprise", and variations such as "comprises" and "comprising", will be understood to imply the inclusion of a stated member, integer or step or group of members, integers or steps but not the exclusion of any other member, integer or step or group of members, integers or steps although in some embodiments such other member, integer or step or group of members, integers or steps may be excluded, i.e. the subject-matter consists in the inclusion of a stated member, integer or step or group of members, integers or steps. The terms "a" and "an" and "the" and similar reference used in the context of describing the invention (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as"), provided herein is intended merely to better illustrate the invention and does not pose a limitation on the scope of the invention otherwise claimed. No language in the specification should be construed as indicating any non-claimed element essential to the practice of the invention.

The term "expression level", as used herein, may refer to the relative expression level, i.e., the expression level of the specific nucleic acid molecule relative to the expression level(s) of one or more reference nucleic acid molecules, or to the absolute expression level, i.e., the actual amount of the specific nucleic acid molecule. In accordance with the present invention, "determining the expression level of a specific nucleic acid molecule in a biological sample" may be "determining the presence or absence of a specific nucleic acid molecule in a biological sample". In one embodiment, the expression level (or the presence or absence) of the specific nucleic acid molecule in the biological sample is indicative of the presence, absence and/or extent/progression of a disease or disorder in a subject from which the biological sample is obtained. In one embodiment, the disease or disorder is cancer, e.g., a cancer as defined herein.

A specific nucleic acid molecule may, according to the invention, be in the form of a molecule, which is single-stranded or double-stranded and linear or covalently closed to form a circle. In one embodiment, the specific nucleic acid molecule is DNA or RNA.

In the context of the present invention, the term "DNA" relates to a molecule, which comprises deoxyribonucleotide residues and is preferably entirely or substantially composed of deoxyribonucleotide residues. "Deoxyribonucleotide" relates to a nucleotide, which lacks a hydroxyl group at the 2'-position of a β-D-ribofuranosyl group. The term "complementary DNA (cDNA)", as used herein, refers to double-stranded DNA synthesized from an RNA template in a reaction catalyzed by the enzyme reverse transcriptase.

In the context of the present invention, the term "RNA" relates to a molecule, which comprises ribonucleotide residues and is preferably entirely or substantially composed of ribonucleotide residues. "Ribonucleotide" relates to a nucleotide with a hydroxyl group at the 2'-position of a β-D-ribofuranosyl group.

In one embodiment, the specific nucleic acid molecule is selected from the group consisting of a specific miRNA, a specific cell-free circulating DNA (e.g., a specific cell-free circulating tumor DNA), a specific mRNA, a specific siRNA and a specific snRNA.

Micro RNAs (miRNAs) are small non-coding RNA molecules consisting of 21 to 23 ribonucleotides, which function in RNA silencing and post-transcriptional regulation of gene expression.

The term "cell-free circulating tumor DNA (ctDNA)" refers to small pieces of tumor DNA that are released by dying tumor cells into the bloodstream. The screening of/for ctDNA allows to detect and follow the progression of a patient's tumor.

Messenger RNA (mRNA) conveys genetic information from DNA to the ribosome, where it specifies the amino acid sequence of the protein products of gene expression.

Small interfering RNA (siRNA) is a class of double-stranded RNA molecules, 20-25 base pairs in length, which interfere with the expression of specific genes with complementary nucleotide sequences (referred to as RNA interference, RNAi).

Small nuclear RNAs (snRNAs) are small RNA molecules with an average length of approximately 150 nucleotides that are, e.g., involved in the processing of pre-messenger RNA (hnRNA) in the cell nucleus of eukaryotic cells. Also included by this term are small nucleolar RNAs (snoRNAs).

In one embodiment, the specific nucleic acid molecule is a specific DNA or RNA molecule, preferably a specific RNA molecule, with a length of less than 500 (deoxy-)ribonucleotides, or less than 400 (deoxy-)ribonucleotides, or less than 300 (deoxy-)ribonucleotides, or less than 200 (deoxy-)ribonucleotides, or less than 100 (deoxy-)ribonucleotides, or less than 50 (deoxy-) ribonucleotides.

In one embodiment, the specific nucleic acid molecule is a specific miRNA, wherein, preferably, the specific miRNA molecule is selected from the group consisting of miR-371a-3p, miR-93-5p, miR-372, miR-373, miR-367 and miR-20a-5p. In one embodiment, the specific miRNA is miR-371a-3p.

The methods according to the present invention allow the detection of specific nucleic acid molecules at the lower detection limit. In one embodiment, the term "lower detection limit" refers to the lower detection limit provided by a PCR-based approach, such as quantitative real-time PCR (qRT-PCR) or digital PCR (dPCR).

In one embodiment, the term "lower detection limit" means that the concentration of the specific nucleic acid molecule in the biological sample is $\leq 1 \times 10^{-11}$ M, or $\leq 1 \times 10^{-12}$ M, or $\leq 1 \times 10^{-13}$ M, or $\leq 1 \times 10^{-14}$ M, or $\leq 1 \times 10^{-15}$ M, or $\leq 1 \times 10^{-16}$ M. In one embodiment, the term "lower detection limit" means that the concentration of the specific nucleic acid molecule in the biological sample is between $1 \times 10^{-11}$ M and $1 \times 10^{-17}$ M, or $1 \times 10^{-12}$ M and $1 \times 10^{-17}$ M, or $1 \times 10^{-13}$ M and $1 \times 10^{-17}$ M, or $1 \times 10^{-14}$ and $1 \times 10^{-17}$ M, or $1 \times 10^{-15}$ and $1 \times 10^{-17}$ M, or $1 \times 10^{-16}$ and $1 \times 10^{-17}$ M.

In one embodiment, the term "lower detection limit" means that the number of the specific nucleic acid molecules in the biological sample is $\leq 10000$, or $\leq 5000$, or $\leq 2500$, or $\leq 1000$, or $\leq 500$, or $\leq 250$. In one embodiment, the term "lower detection limit" means that the number of the specific nucleic acid molecules in the biological sample is between 20 and 10000, or 20 and 5000, or 20 and 2500, or 20 and 1000, or 20 and 500, or 20 and 250. In one embodiment, the term "lower detection limit" means that the number of the specific nucleic acid molecules in the biological sample is between 50 and 10000, or 50 and 5000, or 50 and 2500, or 50 and 1000, or 50 and 500, or 50 and 250. In one embodiment, the term "lower detection limit" means that the number of the specific nucleic acid molecules in the biological sample is between 100 and 10000, or 100 and 5000, or 100 and 2500, or 100 and 1000, or 100 and 500, or 100 and 250.

In one embodiment, the concentrations or numbers of the specific nucleic acid molecule(s) recited herein refer to the concentrations or numbers of the specific nucleic acid molecule(s) in batch A comprising DNA or cDNA isolated/obtained from the biological sample (wherein a specific RNA molecule is converted into the corresponding cDNA molecule). In one embodiment, the concentrations or numbers of the specific nucleic acid molecule(s) recited herein refer to the concentrations or numbers of the specific nucleic acid molecule(s) in the RNA isolated/extracted from the biological sample.

In one embodiment, the independent PCR performed with each of the three or more aliquots in step (ii) of the methods according to the present invention is a preamplification PCR reaction.

Preferred biological samples in accordance with the present invention are selected from the group consisting of body fluid, tissue, cells, cell lysate and cell culture supernatant.

Preferred body fluids are selected from the group consisting of blood serum, blood plasma, seminal plasma, hydrocele fluid, spermatocele fluid, whole blood, urine, amniotic fluid, exudate, sputum, saliva and cerebrospinal fluid. In one embodiment, the body fluid is blood serum.

Tissues are preferably selected from the group consisting of native tissue, snap-frozen tissue and formalin-fixed and paraffin-embedded (FFPE) tissue.

In particular embodiments, the tissue is tumor tissue.

The term "tumor", as used herein, refers to a mass based on neoplastic cell growth and proliferation whether malignant (cancerous) or benign. In one embodiment, the tumor is a solid tumor. In one embodiment, the tumor is derived from a cancer selected from the group consisting of leukemias, seminomas, melanomas, teratomas, lymphomas, neuroblastomas, gliomas, testicular cancer, bladder cancer, rectal cancer, endometrial cancer, kidney cancer, adrenal cancer, thyroid cancer, blood cancer, skin cancer, cancer of the brain, cervical cancer, intestinal cancer, liver cancer, colon cancer, stomach cancer, intestine cancer, head and neck cancer, gastrointestinal cancer, lymph node cancer, esophagus cancer, colorectal cancer, pancreas cancer, ear, nose and throat (ENT) cancer, breast cancer, prostate cancer, cancer of the uterus, ovarian cancer and lung cancer and the metastases thereof. In one embodiment, the cancer is testicular cancer.

In one embodiment, batch A comprises cDNA isolated/obtained from the biological sample.

In one embodiment, step (i) comprises the steps of:
(ia) isolating RNA from the biological sample; and
(ib) converting the RNA isolated in step (ia) into cDNA, thereby providing batch A comprising the cDNA.

Means and methods for the isolation (or extraction) of RNA, e.g., total RNA or miRNA, from a biological sample are known to a person skilled in the art and include commercially available kits, such as the RNeasy Mini Kit and the miRNeasy Mini Kit (both from Qiagen).

The step of converting the RNA into cDNA is preferably performed by reverse transcription (RT) using the enzyme reverse transcriptase. Means and methods for reverse transcription and synthesis of cDNA are known to the skilled person and include commercially available kits, such as the TagMan® microRNA RT Kit (Life Technologies).

Preferred PCR-based approaches in accordance with the present invention are quantitative real-time PCR (qRT-PCR) and digital PCR (dPCR).

In one embodiment, the qRT-PCR is fluorescence-based qRT-PCR comprising the use of a fluorescently labeled probe. In one embodiment, the fluorescently labeled probe consists of an oligonucleotide labeled with both a fluorescent reporter dye and a quencher dye (=dual-label probe). Suitable fluorescent reporter and quencher dyes/moieties are known to a person skilled in the art and include, but are not limited to the reporter dyes/moieties 6-FAM™, JOE™, Cy5® and Cy3® and the quencher dyes/moieties dabcyl, TAMRA™ and BHQ™-1, -2 or -3. Amplification of the probe-specific product causes cleavage of the probe (=amplification-mediated probe displacement), thereby generating an increase in reporter fluorescence. Other suitable fluorescent dyes for use in fluorescence-based qRT-PCR include EvaGreen® and SYBR® Green. In general, the increase of fluorescence in the reaction (measured in real time) is directly proportional to the increase of target amplificates.

dPCR is an alternate method to conventional qRT-PCR for absolute quantification and detection of nucleic acid molecules. dPCR works by partitioning a sample of DNA or cDNA into many individual, parallel PCR reactions; some of these reactions contain the target nucleic acid molecule (positive) while others do not (negative). A single molecule can be amplified a million-fold or more. During amplification, dye-labeled probes are used to detect sequence-specific targets. When no target sequence is present, no signal accumulates. Following PCR analysis, the fraction of negative reactions is used to generate an absolute count of the number of target molecules in the sample, without the need for standards or endogenous controls.

The present invention also provides a method of detecting a disease or disorder in a subject or of determining the extent/progression of a disease or disorder in a subject, the method comprising (a) obtaining a biological sample from the subject, and (b) determining the expression level of a specific nucleic acid molecule in the biological sample with a method as defined herein, wherein the expression level of the specific nucleic acid molecule in the biological sample is indicative of the presence, absence and/or extent/progression of the disease or disorder in the subject. In one embodiment, the disease or disorder is cancer, e.g., a cancer as defined herein.

The term "subject", as used herein, relates to any organism such as a vertebrate, particularly any mammal, including both a human and another mammal, e.g., an animal such as a rodent, a rabbit, or a non-human primate (e.g., a monkey). The rodent may be a mouse, rat, hamster, guinea pig, or chinchilla. Preferably, the subject is a human. In one embodiment, a subject is a subject with or suspected of having a disease or disorder, in particular a disease or disorder as defined herein, also designated "patient" herein.

The present invention is further illustrated by the following examples, which are not to be construed as limiting the scope of the invention.

EXAMPLES

Comparative Example 1 a) RNA Isolation

From serum samples, total RNA was isolated using the QIAGEN miRNeasy Mini Kit according to the manufacturer's instructions with minor modifications for serum samples: for 200 µl serum, 1 ml of QIAzol and 200 µl chloroform were used.

b) cDNA Synthesis

For quantification of miR-371a-3p in serum samples, 6 µl of total RNA were reverse transcribed using the TaqMan® microRNA RT Kit (Life Technologies) and a primer pool consisting of 1 µl each of the stem loop primers for miR-371a-3p and miR-93-5p (for normalization) (Life Technologies, assay IDs: 002124 (miR-371a-3p) and 000432 (miR-93-5p)).

c) Preamplification

Because of the low concentration of RNA/miRNA in serum, a preamplification step was performed prior to qRT-PCR. The preamplification reaction consisted of 4 µl of the reverse transcription (RT) product, 1.12 µl assay (diluted 1:100) each of miR-371a-3p and miR-93-5p, 4 µl 15× Real Time ready cDNA Pre-Amp Master (Roche, Mannheim, Germany) and nuclease free water to add up to a total reaction volume of 20 µl. Preamplification was performed at 95° C. for 1 min, followed by 14 cycles of 95° C. for 15 s and 60° C. for 4 min. The preamplification product was then diluted 1:2 in nuclease-free water and 5 µl of the diluted preamplification product were used for qRT-PCR.

d) Detection of miRNAs by Quantitative Real-Time PCR (qRT-PCR) Using TaqMan® Probes The qRT-PCR reaction consisted of 10 µl of the FASTstart Universal Probe Master (Roche, Mannheim, Germany), 1 µl of the specific assay, and nuclease free water in a total reaction volume of 20 µl. qRT-PCR was performed on the 7500 Fast Real-Time PCR System (Life Technologies) with the following cycling conditions: 10 min at 95° C., then 40 cycles of 15 s at 95° C. and 1 min at 60° C. Relative quantity (RQ) was calculated using the ΔΔCt method.

During the preamplification step, problems often occur, if the determination takes place at the lower detection limit of the qRT-PCR method. The miRNA molecules were pipetted into the cDNA synthesis and transcribed 1:1 into cDNA molecules. That means if there is initially only a small amount of miRNA molecules, this results only in the same small amount of cDNA, too. It is statistically impossible to pipet the same exact amount of cDNA/miRNA molecules into the reaction tube for preamplification again, if the results are to be reproduced during another experiment. The explanation for this is, that, e.g., 10 miRNA or cDNA molecules are present in in the complete reaction tube. If a certain aliquot is pipetted out of that tube into the next reaction tube for the preamplification, because of the statistical probability, it is not possible to take out the same amount of cDNA/miRNA molecules each time. Due to this it is possible that, during one pipetting step, 5 cDNA/miRNA molecules, 8 molecules, 3 molecules or even none of the molecules are transferred into the next preamplification reaction. Own experiments have shown, that this is the reason why reproducible results at the lower detection limit are very difficult or even impossible.

In Table 1, the results of the miRNA analysis of one sample are shown, which was processed after RNA isolation two times (A and B) separately by an individual cDNA synthesis, preamplification and qRT-PCR. Here, it can be clearly seen that the Ct values of the miRNA-371a-3p of the sample in the "A" run differ substantially from those obtained in the "B" run. In contrast, the Ct values of the miRNA-93 of the same sample are almost identical in each run. This results in completely different expression levels for run "A" and "B" of the target miRNA-371a-3p for the same sample. This phenomenon is due to the statistical distribution of the extremely small amount of miRNA molecules: if there are, for example, 1002 miRNA molecules compared to 1005 molecules used for the cDNA synthesis, the difference in the Ct values after preamplification and qRT-PCR is almost invisible. But if there are only 2 compared to 5 molecules pipetted into the preamplification reaction, the difference grows exponentially during the cycles (e.g., 14 cycles) of the preamplification process, and a huge difference in the expression levels respectively Ct values is detected after qRT-PCR. Assuming 100% efficiency of duplication during each cycle, after 14 cycles of preamplification 2 molecules become 16,384 molecules and 5 molecules become 6,103,515,625 molecules.

TABLE 1

Summary of experiments testing the reproducibility of measurements in the qRT-PCR (A and B are different runs of the same sample); Target Name = measured miRNA; Ct = Threshold Cycle; Ct Mean = mean value of the qRT-PCR triplicates).

| Sample Name | Target Name | Ct | Ct Mean |
|---|---|---|---|
| 8594 A | miR-371a-3p | 43.377 | 43.458 |
| 8594 A | miR-371a-3p | 43.520 | 43.458 |
| 8594 A | miR-371a-3p | 43.476 | 43.458 |
| 8594 B | miR-371a-3p | 29.493 | 29.460 |
| 8594 B | miR-371a-3p | 29.479 | 29.460 |
| 8594 B | miR-371a-3p | 29.408 | 29.460 |
| 8594 A | miR-93-5p | 12.780 | 12.791 |
| 8594 A | miR-93-5p | 12.814 | 12.791 |
| 8594 A | miR-93-5p | 12.779 | 12.791 |
| 8594 B | miR-93-5p | 12.580 | 12.631 |
| 8594 B | miR-93-5p | 12.644 | 12.631 |
| 8594 B | miR-93-5p | 12.670 | 12.631 |

These differences can also be seen in Table 2, where a cell line (HT 27), normally expressing miRNA-371a-3p at a very high level, is diluted until the lower detection limit is reached, so that the variations of the Ct values occur.

TABLE 2

Dilution series of a miRNA; Target Name = measured miRNA; Ct = Threshold Cycle; Ct Mean = mean value of the qRT-PCR duplicates; undetectable = no signal during qRT-PCR detectable).

| Sample Name | Target Name | Ct | Ct Mean | Dilution |
|---|---|---|---|---|
| 1) HT 27 (1) | miR-371a-3p | 11.931 | 11.883 | 1:250 |
| 1) HT 27 (1) | miR-371a-3p | 11.836 | 11.883 | |
| 1) HT 27 (2) | miR-371a-3p | 12.101 | 11.998 | |
| 1) HT 27 (2) | miR-371a-3p | 11.896 | 11.998 | |
| 1) HT 27 (3) | miR-371a-3p | 11.985 | 11.975 | |
| 1) HT 27 (3) | miR-371a-3p | 11.964 | 11.975 | |
| 2) HT 27 (1) | miR-371a-3p | 15.277 | 15.310 | 1:2500 |
| 2) HT 27 (1) | miR-371a-3p | 15.342 | 15.310 | |
| 2) HT 27 (2) | miR-371a-3p | 15.394 | 15.386 | |
| 2) HT 27 (2) | miR-371a-3p | 15.378 | 15.386 | |
| 2) HT 27 (3) | miR-371a-3p | 15.426 | 15.419 | |
| 2) HT 27 (3) | miR-371a-3p | 15.412 | 15.419 | |
| 3) HT 27 (1) | miR-371a-3p | 18.596 | 18.582 | 1:25000 |
| 3) HT 27 (1) | miR-371a-3p | 18.569 | 18.582 | |
| 3) HT 27 (2) | miR-371a-3p | 18.552 | 18.548 | |
| 3) HT 27 (2) | miR-371a-3p | 18.544 | 18.548 | |
| 3) HT 27 (3) | miR-371a-3p | 18.797 | 18.758 | |
| 3) HT 27 (3) | miR-371a-3p | 18.720 | 18.758 | |
| 4) HT 27 (1) | miR-371a-3p | 22.241 | 22.258 | 1:250000 |
| 4) HT 27 (1) | miR-371a-3p | 22.274 | 22.258 | |
| 4) HT 27 (2) | miR-371a-3p | 21.958 | 21.924 | |
| 4) HT 27 (2) | miR-371a-3p | 21.889 | 21.924 | |
| 4) HT 27 (3) | miR-371a-3p | 21.961 | 21.958 | |
| 4) HT 27 (3) | miR-371a-3p | 21.955 | 21.958 | |
| 5) HT 27 (1) | miR-371a-3p | 25.487 | 25.516 | 1:2500000 |
| 5) HT 27 (1) | miR-371a-3p | 25.546 | 25.516 | |
| 5) HT 27 (2) | miR-371a-3p | 25.355 | 25.328 | |
| 5) HT 27 (2) | miR-371a-3p | 25.301 | 25.328 | |
| 5) HT 27 (3) | miR-371a-3p | 25.064 | 25.038 | |
| 5) HT 27 (3) | miR-371a-3p | 25.013 | 25.038 | |
| 6) HT 27 (1) | miR-371a-3p | 26.831 | 26.826 | 1:25000000 |
| 6) HT 27 (1) | miR-371a-3p | 26.820 | 26.826 | |
| 6) HT 27 (2) | miR-371a-3p | 34.186 | 34.218 | |
| 6) HT 27 (2) | miR-371a-3p | 34.251 | 34.218 | |
| 6) HT 27 (3) | miR-371a-3p | 29.800 | 29.785 | |
| 6) HT 27 (3) | miR-371a-3p | 29.769 | 29.785 | |
| 7) HT 27 (1) | miR-371a-3p | Undetectable | Undetectable | 1:250000000 |
| 7) HT 27 (2) | miR-371a-3p | Undetectable | Undetectable | |
| 7) HT 27 (2) | miR-371a-3p | Undetectable | Undetectable | |
| 7) HT 27 (3) | miR-371a-3p | Undetectable | Undetectable | |
| 7) HT 27 (3) | miR-371a-3p | Undetectable | Undetectable | |

In another experiment defined amounts of an artificial miRNA, so called cel-miRNA-39, are used exemplarily for the cDNA synthesis. The results are shown in Table 3. Once again, one can see that at about 100 miRNA molecules (approximately 0.0000000002 picomol) major differences regarding the Ct values occur.

TABLE 3 miRNA cel-miRNA-39 dilution at molecular level; Target Name = measured miRNA; Ct = Threshold Cycle; Ct Mean = mean value of the qRT-PCR duplicates; Ct MV = mean value of the three preamplification runs of the same sample; Theoretical Ct = Ct value, that was mathematically determined, based on the value of the highest concentration; ud = Undetectable, no signal during qRT-PCR detectable).

| Sample Name | Number of molecules | Number of molecules [picomol, pmol] | Concentration [M] | Target Name | Ct | Ct Mean | Ct MV | Theoretical Ct |
|---|---|---|---|---|---|---|---|---|
| 1. (1) | | | | cel-miR-39-3p | 4.067 | 4.154 | | |
| 1. (1) | | | | cel-miR-39-3p | 4.241 | 4.154 | | |
| 1. (2) | | | | cel-miR-39-3p | 4.171 | 4.214 | | |
| 1. (2) | | | | cel-miR-39-3p | 4.257 | 4.214 | | |
| 1. (3) | | | | cel-miR-39-3p | 4.334 | 4.308 | | |
| 1. (3) | 1 * 10^8 = 100000000 | 0.00016605388 | 4.15 * 10^−11 | cel-miR-39-3p | 4.283 | 4.308 | 4.23 | 4.20 |

TABLE 3-continued miRNA cel-miRNA-39 dilution at molecular level; Target Name = measured miRNA;
Ct = Threshold Cycle; Ct Mean = mean value of the qRT-PCR duplicates; Ct MV = mean value
of the three preamplification runs of the same sample; Theoretical Ct = Ct value, that was
mathematically determined, based on the value of the highest concentration; ud = Undetectable,
no signal during qRT-PCR detectable).

| Sample Name | Number of molecules | Number of molecules [picomol, pmol] | Concentration [M] | Target Name | Ct | Ct Mean | Ct MV | Theoretical Ct |
|---|---|---|---|---|---|---|---|---|
| 5. (1) | | | | cel-miR-39-3p | 18.928 | 18.961 | | |
| 5. (1) | | | | cel-miR-39-3p | 18.994 | 18.961 | | |
| 5. (2) | | | | cel-miR-39-3p | 19.145 | 19.145 | | |
| 5. (2) | | | | cel-miR-39-3p | 19.145 | 19.145 | | |
| 5. (3) | | | | cel-miR-39-3p | 19.318 | 19.335 | | |
| 5. (3) | $1 * 10^4 = 10000$ | 0.00000001661 | $4.15 * 10^{-15}$ | cel-miR-39-3p | 19.351 | 19.335 | 19.15 | 17.40 |
| 6. (1) | | | | cel-miR-39-3p | 22.598 | 22.578 | | |
| 6. (1) | | | | cel-miR-39-3p | 22.557 | 22.578 | | |
| 6. (3) | | | | cel-miR-39-3p | 23.052 | 23.029 | | |
| 6. (3) | | | | cel-miR-39-3p | 23.005 | 23.029 | | |
| 6. (2) | | | | cel-miR-39-3p | 23.127 | 23.122 | | |
| 6. (2) | $1 * 10^3 = 1000$ | 0.00000000166 | $4.15 * 10^{-16}$ | cel-miR-39-3p | 23.116 | 23.122 | 22.91 | 20.70 |
| 7. (1) | | | | cel-miR-39-3p | 24.781 | 24.822 | | |
| 7. (1) | | | | cel-miR-39-3p | 24.863 | 24.822 | | |
| 7. (2) | | | | cel-miR-39-3p | 27.048 | 27.042 | | |
| 7. (2) | | | | cel-miR-39-3p | 27.037 | 27.042 | | |
| 7. (3) | | | | cel-miR-39-3p | 26.229 | 26.234 | | |
| 7. (3) | $1 * 10^2 = 100$ | 0.00000000017 | $4.15 * 10^{-17}$ | cel-miR-39-3p | 26.240 | 26.234 | 26.03 | 24.00 |
| 8. (1) | | | | cel-miR-39-3p | ud | | | |
| 8. (1) | | | | cel-miR-39-3p | ud | | | |
| 8. (2) | | | | cel-miR-39-3p | ud | | | |
| 8. (2) | | | | cel-miR-39-3p | ud | | | |
| 8. (3) | | | | cel-miR-39-3p | ud | | | |
| 8. (3) | 10 | 0.00000000002 | $4.15 * 10^{-18}$ | cel-miR-39-3p | ud | | ud | 27.30 |
| 9. (1) | | | | cel-miR-39-3p | ud | | | |
| 9. (1) | | | | cel-miR-39-3p | ud | | | |
| 9. (2) | | | | cel-miR-39-3p | ud | | | |
| 9. (2) | | | | cel-miR-39-3p | ud | | | |
| 9. (3) | | | | cel-miR-39-3p | ud | | | |
| 9. (3) | 0 | 0 | 0 | cel-miR-39-3p | ud | | ud | ud | e) Summary

The above data show that the problem of producing reliable results at the lower detection limit is related to the preamplification step. If a preamplification is performed for a sample and this preamplification product is measured using qRT-PCR, then this leads to uniform results each time (see triplicates/duplicates of the qRT-PCR assays in Table 1, Table 2, and Table 3). However, if several preamplifications are performed out of one cDNA reaction tube, and these preamplifications include different amounts of cDNA molecules according to statistics, then this leads to striking differences in the Ct values in the subsequent qRT-PCRs.

Despite the best mixing procedures it is not possible to distribute the small amount of cDNA molecules from the cDNA synthesis in equal parts to the reaction tubes of the preamplification. Afterwards, the error appears and there is a high variation of the Ct values. This is explained by the doubling of the number of molecules with each of the 14 cycles.

Example 1

For the preamplification process, the sample was divided into three reaction tubes after cDNA synthesis. Afterwards, a qRT-PCR was carried out separately with each of the three reaction tubes (see Table 4 and FIG. 1). To consider the deviation of the Ct values and the resulting different expression levels (here exemplarily for miR-371a-3p), the mean value of the three RQ-values was determined mathematically (arithmetic mean) (RQ=relative quantity=expression).

TABLE 4

Results of the qRT-PCR; RQ = relative quantity; Mathematical RQ-MV Ct = mathematical mean value of RQ; Mean = mean value of the qRT-PCR triplicates; undetectable = no signal during qRT-PCR detectable.

| Sample | RQ | Mathematical RQ-MV | Ct Mean 371a-3p | Ct Mean 93 |
|---|---|---|---|---|
| 90 (1) | 0.000 | | undetectable | 11.179 |
| 90 (2) | 9.389 | 3.130 | 30.289 | 11.442 |
| 90 (3) | 0.000 | | undetectable | 11.548 |
| 71 (1) | 14.986 | | 31.809 | 13.637 |
| 71 (2) | 22.193 | 12.393 | 31.249 | 13.644 |
| 71 (3) | 0.000 | | undetectable | 13.651 |

Example 2

Figure 2:
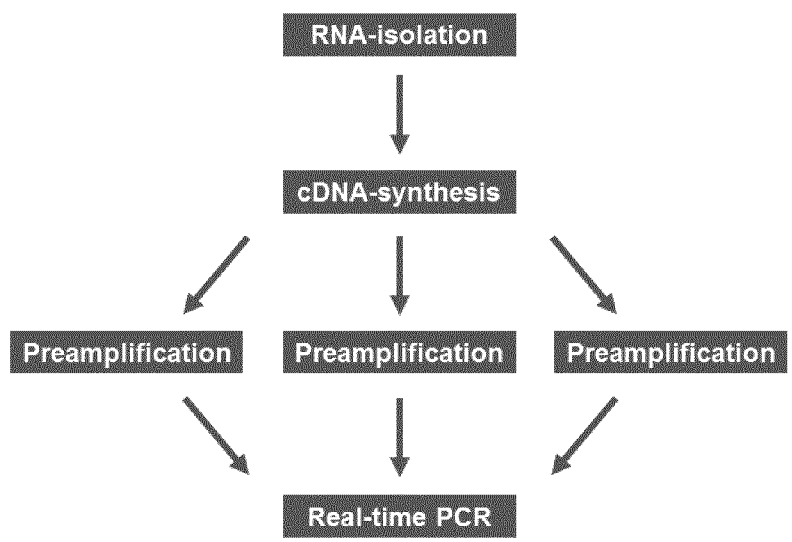
FIG. 2 shows a schematic representation of a method in accordance with the present invention (Example 2). Only one qRT-PCR is carried out with a mixture of equal amounts from three independent preamplification reactions to obtain the measured mean value for the evaluation of the data.

The sample was divided after cDNA synthesis into three reaction tubes for preamplification as in Example 1. After that, an identical volume was taken from each of the three preamplification reaction tubes and pipetted together into one reaction tube and mixed well for a single subsequent qRT-PCR (see FIG. 2).

The triplicate preamplification was made to compensate for the differences in the Ct values and determined expression levels, respectively. These differences can either be compensated by the calculation of the mean value of the RQ values (Example 1=calculated mean value/arithmetic mean) or, as in Example 2, by mixing of the three preamplification reactions and using the mix in the subsequent qRT-PCR analysis, so that a methodic mean value/measured mean for the interpretation of the results is generated. Results of this study are listed in Table 5.

TABLE 5

Results of the qRT-PCR; RQ = relative quantity; Mathematical RQ-MV Ct = mathematical mean value of RQ; Ct Mean = mean value of the qRT-PCR triplicates; undetectable = no signal during qRT-PCR detectable; Zus = sample was processed according to the protocol of Example 2 (methodical mean value).

| Sample | RQ | Mathematical RQ MV (1), (2), (3) | Ct Mean 371a-3p | Ct Mean 93 |
|---|---|---|---|---|
| 80 (1) | 1060.735 | | 24.605 | 12.578 |
| 80 (2) | 1853.232 | | 23.906 | 12.684 |
| 80 (3) | 1365.875 | | 24.292 | 12.630 |
| 80 Zus (1, 2, 3) | 1582.389 | 1426.614 | 24.033 | 12.583 |

TABLE 5-continued

Results of the qRT-PCR; RQ = relative quantity; Mathematical RQ-MV Ct = mathematical mean value of RQ; Ct Mean = mean value of the qRT-PCR triplicates; undetectable = no signal during qRT-PCR detectable; Zus = sample was processed according to the protocol of Example 2 (methodical mean value).

| Sample | RQ | Mathematical RQ MV (1), (2), (3) | Ct Mean 371a-3p | Ct Mean 93 |
|---|---|---|---|---|
| 129 (1) | 154.021 | | 27.944 | 13.133 |
| 129 (2) | 244.851 | | 27.287 | 13.146 |
| 129 (3) | 420.644 | | 26.453 | 13.092 |
| 129 Zus (1, 2, 3) | 278.655 | 273.172 | 27.084 | 13.129 |
| 112 (1) | 0.000 | | | 13.204 |
| 112 (2) | 0.000 | | | 13.336 |
| 112 (3) | 0.000 | | | 13.264 |
| 112 Zus (1, 2, 3) | 0.000 | 0.000 | | 13.373 |
| 90 (1) | 0.000 | | | 11.179 |
| 90 (2) | 9.389 | | 30.289 | 11.442 |
| 90 (3) | 0.000 | | | 11.548 |
| 90 Zus (1, 2, 3) | 2.708 | 3.130 | 32.007 | 11.367 |
| 119 (1) | 79.004 | | 30.596 | 14.822 |
| 119 (2) | 5.524 | | 34.343 | 14.731 |
| 119 (3) | 0.000 | | | 14.874 |
| 119 Zus (1, 2, 3) | 31.989 | 28.176 | 31.995 | 14.917 |

Taken together, the methods of the present invention provide the possibility to analyze specific nucleic acid molecules even at the lower detection limit of ~0.0000000002 picomol in an exact and reliable fashion.

The invention claimed is:

1. A method of determining the level of a target nucleic acid in a biological sample, wherein the target nucleic acid is DNA obtained from the biological sample or cDNA obtained from RNA obtained from the biological sample, the method comprising the steps of:
   (i) providing a batch A comprising the target nucleic acid;
   (ii) providing three or more aliquots of batch A provided in step (i) and performing an independent polymerase chain reaction (PCR) with each of the three or more aliquots in order to amplify the same single target nucleic acid in each of the three or more aliquots, thereby providing three or more batches B comprising the same amplified -target nucleic acid; and
   (iii) mixing equal amounts of the three or more batches B, thereby providing a batch C, and determining the level of the target nucleic acid in batch C by performing a single quantitative real-time PCR (qRT-PCR),
   wherein the level determined in step (iii) corresponds to the expression level of the target nucleic acid in the biological sample.

2. The method of claim 1, wherein the concentration of the target nucleic acid in the biological sample is $<1 \times 10^{-11}$ M, or $<1 \times 10^{-12}$ M, or $<1 \times 10^{-13}$ M, or $<1 \times 10^{-14}$ M, or $<1 \times 10^{-15}$ M, or $<1 \times 10^{-16}$ M, wherein the biological sample is selected from the group consisting of body fluid, tissue, cells, cell lysate and cell culture supernatant.

3. The method of claim 2, wherein the concentration of the target nucleic acid in the biological sample is between $1 \times 10^{-11}$ M and $1 \times 10^{-17}$ M, or $1 \times 10^{-12}$ M and $1 \times 10^{-17}$ M, or $1 \times 10^{-13}$ M and $1 \times 10^{-17}$ M, or $1 \times 10^{-14}$ and $1 \times 10^{-17}$ M, or $1 \times 10^{-15}$ and $1 \times 10^{-17}$ M, or $1 \times 10^{-16}$ and $1 \times 10^{-17}$ M.

4. The method of claim 1, wherein the target nucleic acid is selected from the group consisting of a target miRNA, a target cell-free circulating DNA, a target mRNA, a target siRNA and a target snRNA.

5. The method of claim 4, wherein the target nucleic acid is a target miRNA.

6. The method of claim 5, wherein the target miRNA is selected from the group consisting of miR-371a-3p, miR-93-5p, miR-372, miR-373, miR-367 and miR-20a-5p.

7. The method of claim 1, wherein the biological sample is selected from the group consisting of body fluid, tissue, cells, cell lysate and cell culture supernatant.

8. The method of claim 7, wherein the body fluid is selected from the group consisting of blood serum, blood plasma, seminal plasma, hydrocele fluid, spermatocele fluid, whole blood, urine, amniotic fluid, exudate, sputum, saliva and cerebrospinal fluid.

9. The method of claim 7, wherein the tissue is selected from the group consisting of native tissue, snap-frozen tissue and formalin-fixed and paraffin-embedded (FFPE) tissue.

10. The method of claim 7, wherein the tissue is tumor tissue.

11. The method of claim 1, wherein batch A comprises cDNA.

12. The method of claim 11, wherein step (i) comprises the steps of:

(ia) isolating RNA from the biological sample; and
(ib) converting the RNA isolated in step (ia) into cDNA, thereby providing batch A comprising the cDNA.

13. The method of claim 1, wherein, in step (ii), three aliquots of batch A are provided.

14. The method of claim 2, wherein the body fluid is selected from the group consisting of blood serum, blood plasma, seminal plasma, hydrocele fluid, spermatocele fluid, whole blood, urine, amniotic fluid, exudate, sputum, saliva and cerebrospinal fluid.

15. The method of claim 2, wherein the tissue is selected from the group consisting of native tissue, snap-frozen tissue and formalin-fixed and paraffin-embedded (FFPE) tissue.

16. The method of claim 2, wherein the tissue is tumor tissue.

17. The method of claim 5, wherein the target nucleic acid is a target cell-free circulating DNA, wherein the target cell-free circulating DNA is a target cell-free circulating tumor DNA.

* * * * *